United States Patent [19]

Gandolfi et al.

[11] Patent Number: 4,749,798

[45] Date of Patent: Jun. 7, 1988

[54] FLUORO COUMARINS AS ANTILYMPHOEDEMA AGENTS

[75] Inventors: Carmelo A. Gandolfi; Odoardo Tofanetti; Silvano Spinelli, all of Milan; PierVitto Cipolla, Lodi; Sergio Tognella, Milan, all of Italy

[73] Assignee: Boehringer Biochemia Robin Spa, Milan, Italy

[21] Appl. No.: 808,555

[22] Filed: Dec. 13, 1985

[30] Foreign Application Priority Data

Dec. 21, 1984 [GB] United Kingdom ............... 8432464

[51] Int. Cl.$^4$ ............................................. C07D 311/12
[52] U.S. Cl. ............................... 549/283; 549/399; 514/456; 514/457
[58] Field of Search ........................... 549/283, 399

[56] References Cited

U.S. PATENT DOCUMENTS 3,808,232  4/1974  Hardt et al. ........................ 549/283

OTHER PUBLICATIONS

T. N. Huckerby, J. Mol. Struct., 54, 283 (1979).
O. Danek, Collect. Czech. Chem. Comon., 29, 1035 (1964).
Eygptian Journal of Chemistry; Abdel-Megeid; pp. 463-472, 1977.

Primary Examiner—Jane T. Fan
Attorney, Agent, or Firm—Murray and Whisenhunt

[57] ABSTRACT

A compound of the formula

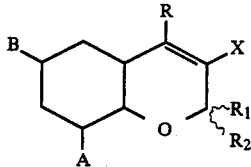

wherein hydrogen, fluorine, chlorine or bromine;
  B is fluorine, or when A is fluorine B may be hydrogen;
  R is hydrogen, $C_1$-$C_8$ branched or unbranched alkyl, $CH_2BR$, $CH_2Cl$ or substituted or unsubstituted phenyl;
  X is hydrogen, chlorine or bromine;
  one of $R_1$ and $R_2$ is hydrogen and the other is hydroxy or $C_1$-$C_7$ branched or unbranched alkoxy unsubstituted or substituted by a dialkyl amino group, or $R_1$ and $R_2$, taken together with the carbon atom to which they are linked, form the group

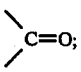

with the proviso that, when R and X are both hydrogen,

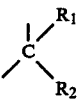

is a

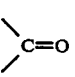

group, and B is fluorine and A is hydrogen is useful as antilimphoedema agent.

4 Claims, No Drawings

FLUORO COUMARINS AS ANTILYMPHOEDEMA AGENTS

The present invention is relative to fluorocoumarins and to their use as antilymphoedema and antiinflammatory agents in man and in animals. It is known that coumarin, 2H-1-benzopyran-2-one, is being investigated extensively in animals (N. B. Piller, J. Lymph. 1, 39 (1977), ibidem 2, 30 (1976) for its observed effects in reduction of swelling associated with high protein edemas.

Toxicological effects have been reported after coumarin administration in various animal species and coumarin has been labeled a category I carcinogen by the Occupational Safety and Health Administration; i.e. see A. J. Cohen, Fd. Cosmet. Toxicol., 17, 277 (1979). As a result of these findings, coumarin has not been permitted for use in food in the United States of America since 1954 and is not currently available for studies in man.

This is of significant clinical importance since several forms of lymphoedema are currently not manageable by medicines. Palliative conservative methods including pressure bandages are instead used. Of course it would be beneficial if suitable drugs for management of such pathologies were available.

Since coumarin administration is effective but not available for therapeutic use, it seems worth looking for coumarin like substances devoid of toxicological side effects and full effective in reducing high protein edemas (see for ex. E. Arrigoni Martelli, Future directions in antirheumatic research, Drug of the Future 7, (9), 663 (1982) and I. H. Hardt and W. A. Ritschel, Arzneim. Forsch./Drug Res. 33 (9) 1662 (1983). Since coumarin is extensively metabolized in man upon first pass through the liver, it should be true that some metabolites, and particularly 7-hydroxy coumarin, also known as umbelliferone, may actually be the active metabolite. That is to say that umbelliferone, one of the main metabolites, may be the pharmacologically active agent (I. H. Hardt and W. A. Ritschel, loc. cit.). In fact, hydroxylation of the coumarin ring is the most important metabolic event in all the animal species. From the qualitative point of view, in vivo and in some animal tissue in vitro, hydroxylation may occur at any position of the coumarin ring but it is more likely in position 3, 7 and 8; hydroxylation in position 4 and 6 is very rare. Furthermore, the metabolic sites of hydroxylation seem to be related to the distribution of the net electron charges in the various atoms of the coumarin molecule.

Quantitative estimation of the metabolites reveals that the amounts of the urinary and faecal metabolites of the coumarin differ significantly in rats, rabbits and man, upsetting the $C_3/C_7$ hydroxy metabolites in favour of the C-7-hydroxylation in man (G. Feuer, The metabolism and biological actions of Coumarins, Progress in Med. Chem. 10, 87–158 (1974), Buttenwords Ed., London), being C-3 hydroxylation practically absent in man.

The present invention is related to coumarins containing fluoro atoms in the phenyl ring, to a method for their preparation and to pharmaceutical compositions containing fluoro coumarins, devoid of mutagenic properties, useful in the treatment of inflammatory diseases, in particular for treatment of lymphoedematous diseases. The compounds of the invention are coumarins of the general formula:

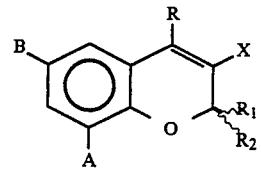

wherein:
A is hydrogen, fluorine, chlorine or bromine;
B is fluorine or when A is fluorine, B may be hydrogen;
R is a member selected from the group consisting of hydrogen, $C_1$–$C_7$ branched or unbranched alkyl, $CH_2Br$, $CH_2Cl$ or a phenyl ring;
X is a member selected from the group consisting of hydrogen, chlorine and bromine;
one of $R_1$, $R_2$ is hydrogen and the other is hydroxy and alcoxy $OR_3$ being $R_3$ a $C_1$–$C_5$ branched and unbranched, lower alkyl substituted or unsubstituted by a dimethylamino or dietylamino group, or $R_1$, $R_2$, taken together with the carbon atom to which they are linked, form the group

with the proviso that when R=X=H,

is a C=O group and one of the groups A, B is fluorine, the other one is different from hydrogen.

The following: 6-fluoro-coumarin, 7-fluoro-coumarin and 8-fluoro-coumarin are chemically known compounds; F. M. E. Abdel-Megeid, M. A. F. El-Kaschef and A. A. G. Ghattas (Egypt. J. of Chem., 20, (5) 453 (1977)) described the synthesis of 6-fluoro and 8-fluoro coumarins starting from the corresponding 6- and 8-amino coumarins by thermal decomposition of the corresponding dry diazonium fluoborate salt. They reported also that the interest in 6- and 8-fluoro coumarins was due to the growing and promising importance of the fluorinated heterocyclic compounds in industry and in view of their chemotherapeutic value. In fact, they describe the use of the 6-fluoro coumarin in the synthesis of 5 and 7 nitro-6-fluoro coumarin, in the preparation of 5-fluoro salicilic acid after fusion with potassium hydroxyde and in the synthesis of the 5-fluoro-2-hydroxy-cinnamic acid by treatment with aqueous potassium hydroxide. 6-fluoro coumarin, when catalytically hydrogenated, gave 3,4-dihydro-6-fluoro coumarin, which, on hydrolysis with aqueous potassium hydroxide, gave β-(2-hydroxy-5-fluorophenyl)-propionic acid, (fluoro-melilotic acid). This last product could be of biological value due to the reported activity of 3-fluoro-4-hydroxyphenylacetic acid "Capacin" "as having therapeutic effect in mild hyperthyrodism".

T. N. Huckerby (J. Mol. Struct., 54, 283 (1979)) described the synthesis of 7-fluoro coumarin by reaction of m-fluoro-phenol with malic acid in concentrated $H_2SO_4$. Aim of this work was only the spectral characterization of 7-fluoro coumarin from a 20-MHz study of chemical shifts, carbon-proton and carbon-fluorine coupling constants.

In fact, T. N. Huckerby (loc. cit.) reported that "almost no investigations have been made on compounds containing the 2H-1-benzopyran-2-one ring system with a fluorine substituent". The only monofluoro coumarin so far described appears to be 3-fluoro-coumarin (E. D. Bergmann and F. Shahak, J. Chem. Soc., 4033 (1961)). No monosubstituted coumarins bearing a fluorine in the benzenoid ring have hitherto been reported, although the synthesis of 6- and 7-fluoro-4 hydroxy coumarin has been described (O. Danek, Collect. Czech. Chem. Comon. 29, 1035 (1964)).

Particularly preferred compounds of the invention are fluoro coumarins where a fluorine atom present in the benzenoid ring is in para and/or in ortho position as regards to the oxygen ring directly linked to the phenyl ring. Also disubstituted fluoro compounds are preferred compounds when the two fluorine atoms are situated in o- and p-positions with comparison to oxygen phenolic atom.

Particular examples of preferred compounds of the invention are the followings:
6-fluoro-4-methyl-2H-1-benzopyran-2-one (6-fluoro-4-methyl-coumarin)
6-fluoro-4-ethyl-2H-1-benzopyran-2-one (6-fluoro-4-ethyl-coumarin)
6-fluoro-3-bromo-2H-1-benzopyran-2-one (6-fluoro-3-bromo-coumarin)
6-fluoro-3-chloro-2H-1-benzopyran-2-one (6-fluoro-3-chloro-coumarin)
6-fluoro-4-methyl-3-chloro-2H-1-benzopyran-3-one
6-fluoro-4-chloromethyl-3-chloro-2H-1-benzopyran-2-one
6,8-difluoro-2H-1-benzopyran-2-one
6-fluoro-4-phenyl-2H-1-benzopyran-2-one
6-fluoro-4-methyl-3-bromo-2H-1-benzopyran-2-one
6-fluoro-4-bromomethyl-3-bromo-2H-1-benzopyran-2-one
8-fluoro-3-bromo-2H-1-benzopyran-2-one
6-fluoro-2$\xi$-hydroxy-2H-1-benzopyrane
6-fluoro-2$\xi$-hydroxy-2H-1-benzopyrane
6-fluoro-2$\xi$-ethoxy-2H-1-benzopyrane
6-fluoro-2$\xi$-(2'-dimethylaminoethoxy)-2H-1-benzopyrane
6-fluoro-2$\xi$-(2'-diethylaminoethoxy)-2H-1-benzopyrane
6-fluoro-2$\xi$-isopropoxy-2H-1-benzopyrane
6-fluoro-3-bromo-2$\xi$-hydroxy-2H-1-benzopyrane
6-fluoro-3-bromo-2$\xi$-methoxy-2H-1-benzopyrane The compounds of the invention are prepared by a process comprising the reaction, in presence of strong acids such as sulphuric and methane sulphonic acid, of a fluorophenol of the general formula II:

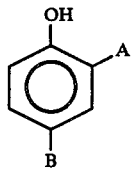

wherein A and B are as above mentioned with a compound of the general formula III:

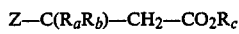

Z—C($R_a R_b$)—CH$_2$—CO$_2 R_c$ wherein Z is a member selected in the group consisting of a carboxylic group, $C_1$-$C_7$ lower alkyl group, branched or unbranched, substituted and unsubstituted phenyl;
one of $R_a$, $R_b$ is hydrogen and the other is hydroxy, acyloxy and together $R_a$, $R_b$ are oxygen;
$R_c$ is hydrogen, methyl or ethyl;
to give a compound of the general formula Ia:

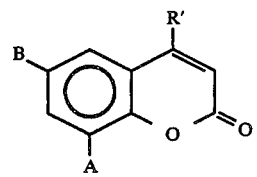

wherein A and B are as above defined and R' is a member selected in the group consisting of hydrogen, a $C_1$-$C_7$ branched or unbranched alkyl, substituted and unsubstituted phenyl.

Compound Ia may be then halogenated with chlorine, bromine or iodine to give a compound of formula IV:

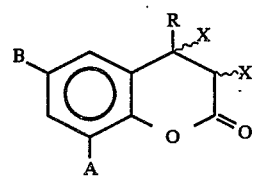

(wherein A, B, R are as above defined and X is chlorine, bromine or iodine) which is in turn dehydrohalogenated to give compounds of formula Ib

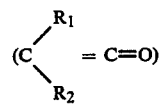

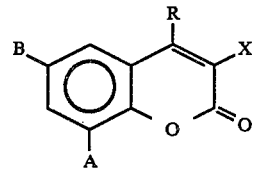

wherein A, B, R, X are as above defined.

Reduction of compounds Ib yields a lactol compound of formula Ic ($R_1$=H, $R_2$=Ri or vice versa, where Ri is hydrogen which can be converted in the corresponding acetal ethers of formula Ic ($R_1$=H, $R_2$=$OR_i$ or vice versa wherein $R_i$ is a $C_1$-$C_5$ alkyl) by treatment with alcohols of formula $R_3$OH wherein $R_3$ is a $C_1$-$C_5$ alkyl, optionally substituted by a dimethyl- or diethylamino group.

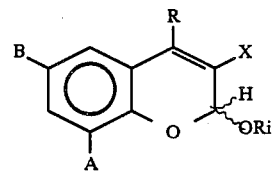

Alternatively, the compounds of formula IV can be reduced to the lactols of formula V:

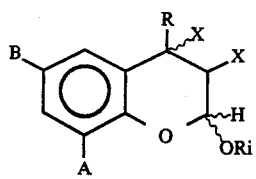

wherein A, B, R, X Ri are as above defined, which can be reacted with an alchol of formula R₃OH to give the corresponding acetal ethers, and then dehydrohalogenated to give the acetal ethers of compounds Ic.

The enclosed reaction scheme illustrates the preparation of the compounds of the invention.

In the dehydrohalogenation of the compounds of formula IV to obtain the compounds of formula Ib, the organic base preferably used is an amine as triethylamine, pyridine, collidine, dimethylaniline and dialkylaniline, diazobicycloundecene, diazobicyclononene. Every amine can be useful and the amine preferably selected is a low cost amine.

The solvents can be ethers, esters such as ethylether, dioxane, dimethoxyethane, tetrahydrofuran, ethyl acetate; methylene chloride, 1,2-dichloroethane; alcohols such as ethanol, 2-propanol, 1-propanol and ketones such as acetone, methyl ethylketone. An inorganic base such as potassium, sodium or ammonium acetate, may also be used, optionally in heterogeneous phase in the above solvents.

During this reaction, concomitant halogenation occurs at the benzylic positions of the compounds of for-

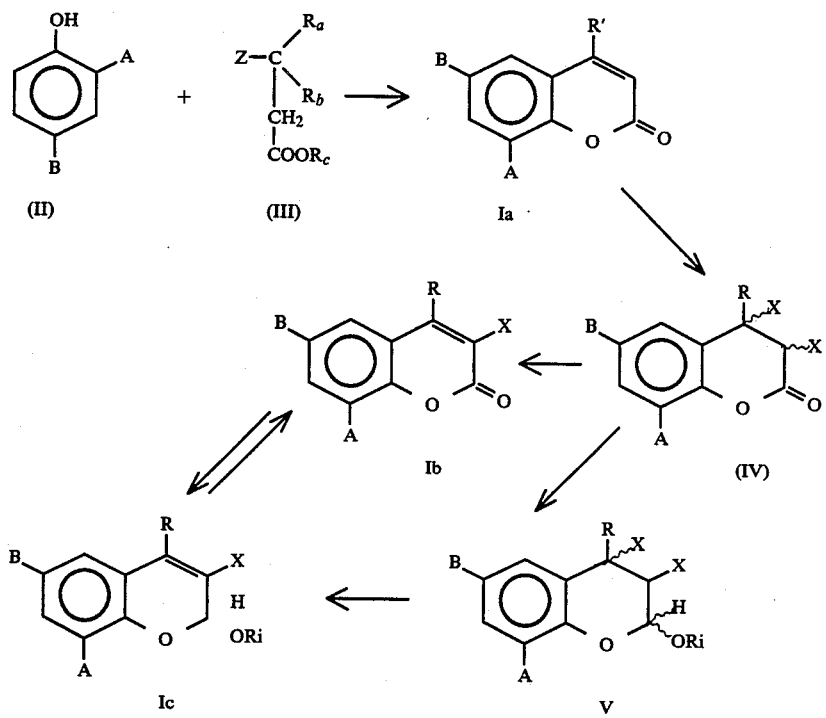

The reaction of the phenol of formula II with a compound of formula III is carried out in the presence of a strong acid such as sulphuric acid and methane sulphonic acid. The preferred acid is concentrated sulphuric acid. The mixture can be heated at a temperature from 40° to 130° C. for a period ranging from ten minutes to 3 hours. Preferably, a compound of formula III is added to a preheated mixture of a compound of formula II in sulphuric acid in small portions and the reaction time is half an hour. The preferred temperature is 95°-100° inner temperature, but prolonged times are not critical for yields.

The compounds of general formula IV are obtained starting from the compounds of formula Ia by treatment with an excess of the halogen in an inert solvent such as methylene chloride, trichloromethane, 1,2-dichloroethane, carbon tetrachloride and mixture of them. The reaction temperature is comprised between room temperature and the boiling temperature of the solvent. Lightening with sun and artificial light favours the shortening of the reaction time which can be variable from ten minutes to ten hours.

mula Ia, where R is an alkyl group. When desired, an optional removal of the benzylic halogen atom is selectively obtained, after the dehydrohalogenation process, by treatment with equimolecular amounts of zinc borohydride at room temperature in an inert solvent such as ethyl ether, dimethoxyethane and their mixtures. The selective reduction of the lactone group of the compounds of formula Ib can be made by treatment with diisobutyl aluminium hydride. Other reagents can also be profitably used such as sodium diethylhydro aluminate and sodium bis(2-methoxyethoxy)-aluminium hydride. The reaction occurs without affecting the conjugated double bond when carried out at a temperature below −40° C. using stoichiometric amount of the above mentioned reagents also if a molar excess is compatible with the reaction. The lactols of formula Ic, where R is hydrogen, and particularly in the cases where X is hydrogen, are obtained, at the end of the reduction reaction, by cautious addition of water to destroy the excess of reduction reagent and to decompose the aluminate intermediates. In fact, direct addition of alcohols unexpectedly yields acetalic ethers. The same acetalic ethers can be optionally prepared starting from the lactols of formula Ic, by reaction with the alcohols of formula $R_3OH$ in the presence of a Lewis' catalyst such as, for ex., boron trifluoride-p-toluensulphonic acid.

In any case, the protection of the double bond during the reduction of the lactone group of the compounds of formula Ib to give the compounds of formula Ic can be optionally obtained submitting the intermediate dihalo compounds of formula V to the reductive procss. In fact, under the experimental conditions above described, compounds of formula V are obtained, which are optionally dehydrohalogenated to give the compounds of formula Ic, where X is halogen or, alternatively, the compounds of formula V can be optionally reacted with an iodide such as NaI, KI, to give the compounds of formula Ic, where X is hydrogen.

The preferred solvent for the dehalogenation reaction is acetone. Other solvents can be used such as dimethylformamide, dimethylacetamide, formamide and their mixtures.

All the lactols of formula Ic, can be optionally converted into the lactones of formula Ib by treatment with $MnO_2$ in a halogenated solvent such as $CHCl_3$, $CH_2Cl_2$, $C_2H_4Cl_2$ and/or by oxidation, using Moffatt's conditions.

By reaction of p-fluoro-phenol with $C^{14}$-malic acid, $C^{14}$-labelled 6-fluoro coumarin was obtained which was used for metabolic studies.

In order to evaluate its aptitude to be hydroxylated, two types of experiences of metabolization were made.

Using the method reported by T. C. Butler et al. (Arch. Intern. Pharmacod. Ther., 228, 4 (1977)), labelled $C^{14}$-6 fluoro coumarin was incubated with dog liver microsomes. At the end of the experiment, the analysis of the extracts did not reveal any by-product, 6-fluoro-coumarin (80% recovery) being the only product present in the extracts. Consequently, this experiment demonstrated that 6-fluoro coumarin was not metabolized by cytochromes.

In a second experiment, $C^{14}$-labelled 6-fluoro coumarin was administered by oral route to rabbits and faeces and urines were collected during a period of 24 hours. As it is usual for metabolic studies, the excreta were treated by β-glucoronidase and aryl sulfatase and extracted by methylene chloride in a little acid medium. The recovered (80%) radioactive material was analyzed by TLC and HPLC and it was found to be unchanged 6-fluoro-coumarin. In these studies, labelled 6-fluoro coumarin having a 1 Ci/mole specific radioactivity was used. It was therefore evident that, after introduction of a fluorine atom at C-6 site of the coumarin moiety, the 6-fluoro coumarin molecule becomes totally resistant to the hydroxylation reactions in opposition to the coumarin which, in similar experimental conditions, was metabolized by hydroxylation and also by δ-lactone ring opening.

Comparative mutagenic studies have shown that 6-fluoro coumarin and the other compounds of the invention are not mutagenic whereas coumarin is mutagenic.

The introduction of a fluoro atom at C-6 position of the benzopyran-2-one ring makes the 6-fluoro coumarin (6-fluoro-2H-1-benzopyran-2-one) totally resistant to the metabolic hydroxylation. In similar experimental conditions, coumarin, lacking the fluoro atom, is metabolized by hydroxylation and by δ-lacton ring opening.

Comparative mutagenic studies have shown that 6-fluoro coumarin and the other compounds of the present invention, where the benzene rings of the 2H-1-benzopyran-2-one moiety are at least substituted by one fluoro atom, are not mutagenic substances whereas coumarin is mutagenic.

In Can. J. Genet. Cytol., 22, 679 (1980)—report by D. R. Stolz and P. M. Scott—it is described that performing Ames test in S-strains of *S. typhimurium* (TA 1535, TA 1537, TA 1538, TA 98, TA 100) in the absence and presence of liver homogenate from aroclor 1524-induced rats, coumarin induces mutagenic responses, particularly with TA 1000 at 5 and 10 μm/plate. The A.A. conclude that coumarin and some structural analogues "may indeed possess carcinogenic effects".

Moreover, in a subsequent report by R. L. Norman and A. W. Wood (Proced. Ass. Canc. Res. 22, 433 (1981) coumarin is reported again to be a weak mutagenic substance, using a similar experimental procedure. On the contrary, no mutagenic property is evident when 6-fluoro coumarin and the other fluoro-2H-1-benzopyran-2-ones of the present invention are submitted to the Ames test using *S-typhimurium* TA 1535, TA 1537, TA 1538, TA 98 and TA 100. To confirm further the absence of any mutagenic properties, the fluoro compounds of the present invention are also submitted to the following tests: (a) forward mutation in *S. Pombae*, (b) mitotic genic conversion in *S. cerevisiae*, (c) gene mutation test in somatic mammalian cells cultured in vitro. No kinds of effects are noticed using 6-fluoro coumarin and the other fluoro-2H-1-benzopyran-2-ones of the present invention, whereas coumarin is a positive responder. The compounds according to the invention are endowed with several pharmacological properties, as it will be apparent from the tests reported hereinafter. The fluoro coumarins of the invention cause increasing degree of proteolysis. Ability of the 6-fluoro coumarin itself, and the other compounds of the invention, to increase proteolysis by mouse peritoneal macrophages is shown by using the testing procedure reported by T. Bolton and J. R. Casley-Smith, Experimentia, 31, 275 (1975).

TABLE 1

| Proteolys vs macrophages; expressed as mM glycin | | | |
|---|---|---|---|
| Dose of 6-fluoro coumarin mg/kg (i.p. route) | N. of mice | Mean ICA-soluble fragm. (24 h–0 h) x. $10^6$ cell | Standard error | Significance of difference from control |
| 0 | 10 | 0.12 | 0.037 | |
| 3.12 | 10 | 0.22 | 0.066 | NS |
| 6.25 | 10 | 0.19 | 0.058 | NS |
| 12.5 | 10 | 0.29 | 0.062 | * |
| 25 | 10 | 0.37 | 0.044 | ** |
| 50 | 10 | 0.34 | 0.052 | * |
| 100 | 10 | 0.40 | 0.073 | ** |

NS implies p > 0.05; *implies 0.05 > p > 0.01; **implies 0.01 > p > 0.01

As it is reported in table 1, 6-fluoro coumarin at the dosage level above the 6.25 mg/kg shows increasing degree of proteolysis, significantly greater than the control. At the higher doses, the threefold increase in proteolysis favourably compares with a 2.2 fold increase produced by similar doses of coumarin.

Stimulation of protein digestion of the protein rich-edemas, induced by the 6-fluorocoumarin, starts from the dose of 12,5 mg/kg and the compound is clearly effective at the dose of 25 mg/kg.

Similar results are obtained with other compounds of the invention. The obtained increase of the proteolytic activity is so evident to confirm their efficacy and their mechanism of action.

Due to the great standard error, many replications are necessary in order to obtain reliable dose-response curves. Nevertheless, for screening purposes, only one dose 50 mg/kg (i.p. route) was investigated and table 2 shows comparative potency ratio.

TABLE 2

| Comparative activity in the proteolytic test | | | |
|---|---|---|---|
| 2H—1-benzo-pyran-2-ones | | Potency ratio. | |
| Coumarin | 1 | 6,8-difluoro | 1.45 |
| 6-fluoro | 11.5 | 4-methyl-6-F | 1.78 |
| 3-Cl—6-fluoro | 1.4 | 3-Br—6-fluoro | 1.75 |
| Other compounds: | | | |
| 6-fluoro-2H—1-benzopyran-2ξ-ol | | | 1.45 |
| 6-fluoro-2H—1-benzopyran-2-ζ-isopropoxy | | | 1.61 |
| 10 replication. Administration by i.p. route in sesame oil. | | | |

6-fluoro coumarin and the compounds of the invention are also effective in the management of the acute inflammation. In fact, 6-fluoro coumarin and related compounds as 3-bromo-6-fluoro, 4-methyl-6-fluoro-2H-1-benzopyran-2-ones, 6-fluoro-2-isopropoxy-2H-1-benzopyrane, 6-fluoro-2ξ-methoxy-2H-1-benzopyrane, 6-fluoro-3-bromo-2ξ-methoxy-2H-1-benzopyrane and 6-fluoro-2ξ-hydroxy-2H-1-benzopyrane reduce carrageenan induced edema of the rats hind paw at all the times (1; 3; 4 and 5 h) after application of the irritative stimulus. The compounds appear to be at least 1.5–2.5 times more active than coumarin.

TABLE 3

| % Reduction of the edema by carrageenan in the hind of rats at different times | | | | | |
|---|---|---|---|---|---|
| Compounds dose in mg/kg | 0.76 | 1.55 | 3 h 3.12 | 6.25 | 5 h 3.12 |
| Coumarin | n.e. | 23 | 53 | 78 | 53.4 |
| 6-fluoro-2ξ-methoxy-2H—1-benzopyran | 58 | 70 | 79 | 84 | 87 |
| 6-fluoro-3-bromo-2ξ-hydroxy-2H—1-benzopyran | 65 | 72 | 88 | 87 | 84 | n.e. = not evaluable

Results obtained with some representative lactol compounds of the invention (such as 6-fluoro-2ξ-methoxy-2H-1benzopyrane and 6-fluoro-3-bromo-2ξ-hydroxy-2H-1-benzopyrane) are reported in table 3.

The carrageenan edema test proposed by Winter C. A., Risley A., Noss G. W. (Proc. Soc. Exp. Biol., 101, 544, 1962) was used.

The compounds, administered i.p. 30' before the carrageenan as suspension in 1% aqueous carboxymethylcellulose homogeneized by ultrasounds, were compared with coumarin at different dose-levels on 6 animal groups. The percent reduction of the rat hinwd paw edema was evaluated at different times.

Results were confirmed in a second experiment.

Reduction of the burning induced oedema test has been also used to evidentiate the antiinflammatory activity and the proteolytic mechanism of action of the compounds of the invention. 18 hours-fasted Sprague-Dawley male rats, body weight: 170–220 g, are used in this testing procedure. The animals are divided into five animal groups and the volume (in ml) of the posterior hind paws is measured before these paws are burnt by immersion for 22 seconds in 55° C. heated water. 15 minutes after burning, the animals are treated, by oral route, with different dosages of the investigated compounds and placebo. The volume of paws is measured 6, 12 and 18 hours after burning and the increased volume of the paws is evaluated. Results at the 12th hour with 6-fluoro coumarin are indicatively reported in table 4.

TABLE 4

| | Paw volume | | | |
|---|---|---|---|---|
| mg/kg | Basal value | 12 h value | DV | % inhibition |
| — | 1.452 | 2.352 | 0.9 | |
| 12.5 | 1.348 | 2.207 | 0.86 | no sign |
| 25.0 | 1.504 | 2.060 | 0.56 | 37 |
| 50.0 | 1.464 | 1.760 | 0.29 | 67 |
| 1000.0 | 1.416 | 1.676 | 0.26 | 71 |

Coumarin, dosed at 50 mg/kg, appears to be about 2 times less active than 6-fluoro coumarin, affording a 35% inhibition. Other compounds of the invention, such as 3-bromo-6-fluoro-2H-1-benzopyran-2-one, 4-methyl-6-fluoro-2H-1-benzopyran-2-one and the lactolethers 6-fluoro-2-isopropoxy-2H-1-benzopyran, 6-fluoro-2-methoxy-2H-1-benzopyran and 6-fluoro-3-bromo-2-methoxy-2H-1-benzopyran proved to be equiactive (0.85–1.5 times) than the 6-fluoro coumarin.

Finally, the compounds of the invention are able to induce re-absorption of the total citrated blood when blood is injected in the right ear of New Zealand rabbits. 12 hours after blood inoculation into ear, the animal were randomized and treated with scalar doses of the investigated compounds administered for 4 days by oral route. The blood-dot areas are evaluated and compared with the areas of the control animals treated with placebo only. In table 5 are reported some experimental results.

TABLE 5

| % reduction of blood-dot area after 4 days | | |
|---|---|---|
| Substance | mg/kg pro die | % reduction |
| placebo | — | 20.3 |
| coumarin | 50 | 67.31 |
| 6-fluoro | 25 | 64.13 |
| 6-fluoro | 50 | 92 |
| 4-methyl-6-F | 50 | 65 |
| 3-bromo-6-fluoro | 50 | 69 |
| 6-fluoro-2ξ-ol-2H—1-benzopyran | 40 | 59 |

The results of this investigation further support the efficacy of the 6-fluoro coumarin and the more strictly related compounds in the pharmacological treatment of the different kind of edema. The ability to stimulate the protein digestion by macrofages makes them particularly suited for the treatment of high protein edemas.

The compound of the invention does not induce any kind of modifications on coagulation factors. It is known the report by Schofield (Can. Vet. Rec. 3, 74 (1922) in which some anticoagulant activites for coumarin and its derivatives, particularly dicoumarol, are described. A lot of experimental work further confirm this anticoagulant effect (see for ex., G. Feuer et al., Progr. in Med. Chem. 10, 85–153 (1974).

6-fluoro coumarin and the compounds of the invention administered by oral route for 2 consecutive days, in comparison with equimolecular doses of coumarin and dicoumarol, are not able to modify DPTT, Hepato quick and clotting time. On the contrary, coumarin moderately influences Hepato quick (in decreasing way) whereas dicoumarol, as expected, presents a very strong effect on DPTT and Hepato quick. Therefore, for these reasons, the compounds of the invention are useful in treatment and prevention of inflammatory diseases and particularly in treatment and prevention of edematous status and specially in edemas rich in proteins of high molecular weight, for ex.: (a) inflammatory edemas, independently on the nosologic derivation; (b) post-surgical edemas; (c) lymphoedemas; (d) edemas coming from damages of the lymphatic and/or venous system.

The efficacy and good tolerability of the compounds of the invention are also proved by means of preliminary experiments in humans. So, a very restricted number of selected male and female patients, affected by primary and secondary lymphoedemas, with intact renal and hepatic functions, was treated with the compounds of the invention, particularly with 6-fluoro coumarin.

The compound of the present invention, 6-fluoro coumarin, was asministered in capsules dosed at 50 mg of the active ingredient. In the absence of any other therapeutic treatment, the selected schedule of treatment foresees administration of capsules, many times pro die.

The preferred protocol is one capsule pro die for 4 days; the dosage is then increased to 2 capsules pro die for 5 days, if the compound of the invention is well tolerated. A further increase to 3 and 4 capsules pro die is also foreseen and then, this regimen is continued for eight days at least, up to thirty days of overall treatment with the compound, if clinical and biological adverse advices are not revealed.

The diagnostic parameters investigated are: general and gastric clinical tolerability; number of red blood cell, leukocites, neutrophiles and platelets; haemoglobin concentration, $\gamma$-glutamyl transpeptidase; serum creatinine and volume of edema.

In the 10 treated patients, the tolerability appears to be excellent at all the dosages investigated. In 4 of the 10 patients, a significant reduction of the oedema volume is also present.

The compounds according to the invention which are useful in human and veterinary therapy, can be administered by oral, intramuscular, subcutaneous, topical (e.g. buccal such as sublingual and cutaneous), transepidermal, rectal routes in doses ranging from 0.1 to 75 mg/kg/day, depending on age, weight and condition of the patient.

They may be given orally in tablets, capsules, drops or syrups, rectally in suppositories, parenterally in solutions or suspensions given subcutaneously or intramuscularly. Local applications by ointment, cream and pressure bandages are also preferred administration routes. Pharmaceutical compositions of the compounds according to the invention may be prepared conventionally using common carriers and/or diluents. Conventional carriers and diluents include water, gelatin, lactose, dextrose, sucrose, mannitol, sorbitol, cellulose, talc, stearic acid, calcium and magnesium stearate, glycols, starch, arabic, tragacanth gum gum alginic acid, alginates, lecithin, polysorbates, vegetable oils. According to a further feature of the present invention a formulation is provided comprising, as the active ingredient, at least one compound of the formula I, together with at least one pharmaceutical carrier or excipient. These pharmaceutical formulations may be used in the treatment or prophylaxis of the above referred conditions. The carrier, of course, must be "acceptable" i.e. must be compatible with the other ingredients of the formulation and not deleterious to the recipient thereof. The carrier may be a solid or a liquid and it is preferably formulated with a compound of formula I as an unit-dose formulation; for ex. a tablet, which may contain from 0.5% to 95% by weight of the active ingredient. Formulations suitable for oral administration may be presented as discrete units such as capsules, cachets, lozenges or tablets each containing a predetermined amount of the active compound; as powders or granules; as solutions or suspensions in aqueous or non-aqueous liquids; as oil-in-water emulsions; or as water-in-oil liquid emulsions. Such formulations may be prepared by any of the methods of pharmacy but all methods include the step of bringing into association the active ingredient with the carrier which comprises one or more appropriate ingredients. In general, the formulation may be prepared by uniformly and intimately admixing the active ingredient with liquids or finely divided solid carriers or both, and then, if necessary, shaping the product into the desired presentation. For ex. a tablet may be prepared by compression or moulding a powder or granules of the active ingredient, optionally with one or more accessory ingredients. Compressed tablets may be prepared by compressing, in a suitable machine, the active ingredient in a free-flowing form such as a powder or granules optionally mixed with a binder, lubricant, inert diluent, surface active or dispersing agent(s). Moulded tablets may be made by moulding in a suitable machine the powdered active ingredient moistened with an inert liquid diluent.

Formulations suitable for buccal (e.g. sub-lingual) administration include lozenges comprising the active ingredient compound in a flavoured bases, e.g. sucrose and acacia or tragacanth; and pastilles comprising the active ingredient in an inert base such as gelatin and glycerin; or sucrose and acacia.

Formulations suitable for rectal administration are preferably presented as unit-dose suppositories. These may be prepared by admixture of the active ingredient with one or more conventional solid carriers, forming the suppository base for ex. cocoa butter, and shaping of the resulting mixture.

Formulations suitable for cutaneous use are preferably presented as lotions, gels and ointments. The lotions may by prepared by admixture of a compound of formula I in a hydroalcoholic medium.

The gels may be prepared with water or anhydrous in conventional way by mixing a compound of formula I with carboxypolymethylene and/or carboxymethylcellulose. Anhydrous gels are prepared using glycerin, polyethylene glycols, carboxypolymethylene and their mixture. A penetration enhancer such as dimethylsulphoxide can be also added. Emulsions are made in conventional way using water and fatty excipients such as lanolin, paraffin oil and wax in presence of surfactans and emulsifying agents such as polysorbate.

The invention is illustrated by the following non limiting examples wherein the abbreviation DIBAH refers to diisobutylaluminium hydride.

EXAMPLE 1

A solution of p-fluoro-phenol (200 g) in sulfuric acid (260 ml) is heated at 100° C. and malic acid (300 g) is added in 4 portions, every 8 minutes. The heating is continued for additional 10 minutes and the reaction mixture is poured in a stirred mixture of ice (1.5 kg), water (800 ml), 28% aqueous ammonia (640 ml) and ethyl acetate (1.5 l). The aqueous layer, weakly acid (pH 2.5-3), is separated and extracted with ethyl acetate (2×50 ml). The collected organic phases are washed with water (3×50 mL), 10% aqueous K$_2$HPC$_4$ (3×50), water (2×25) and dried on Na$_2$SO$_4$. Evaporation of solvent allows to crystallize 6-fluoro-2H-1-benzopyran-2-one (42 g), m.p.=161.5°-3° C.

EXAMPLE 2

A stirred mixture of p-fluoro-phenol (200 g), sulphuric acid (260 ml) and malic acid (300 g) is heated at 110° C. and maintained at this temperature for 2 hours. The mixture is poured in stirred water and ice (3 l). The aqueous phase is decanted and the precipitate is dissolved in ethylacetate. The organic phase is washed until neutral, dried on Na$_2$SO$_4$ and evaporated to dryness. The residue is crystallized from acetone yielding 61 g of 6-fluoro-2H-1-benzopyran-2-one, m.p.=160°-162° C.

EXAMPLE 3

Bromine (64 g) is added to a solution of 32.8 g of 6-fluoro-2H-1-benzopyran-2-one in chloroform (450 ml) and refluxed under artificial white light for 1 hour. The reaction mixture is cooled, the excess of bromine is destroyed by washing with aqueous 10% sodium sulphite. The organic phase, after further washing until neutral, is dried on Na$_2$SO$_4$ and the solvent is evaporated to dryness. The crude material is crystallized from ethylether affording 29.9 of 6-fluoro-3,4-dibromo-2H-1-dihydro-benzopyran-2-one, m.p.=110°-112° C. I.R.

1760 cm$^{-1}$. The liquor waters are diluted with pyridine (25 ml) and stirred at room temperature for 4 hours. The organic phase is partitioned with 4N H$_2$SO$_4$, separated, washed with water, dried on Na$_2$SO$_4$. After evaporation of the solvent, the residue is crystallized from acetone-ethyl acetate yielding 6.5 g of 6-fluoro-3-bromo-2H-1-benzopyran-2-one, m.p.=160°-162° C. I.R.

1720 cm$^{-1}$

EXAMPLE 4

A 0.62M solution of chlorine in carbon tetrachloride (320 ml) is added to a solution of 6-fluoro-2H-1-benzopyran-2-one in chloroform (300 ml) and the mixture is heated at reflux temperature under lightening with a 160 Watt lamp. After 3 hours, the reaction is stopped, the excess reagent is destroyed with aqueous sodium sulfite, the organic phase is worked in the usual way and a crude material is obtained by evaporation to dryness of the solvents. Crystallization from ethyl ether yielding 16.9 g of 6-fluoro-3,4-dichloro-2H-1-dihydro-benzopyran-2-one, m.m.=91°-92° C.

EXAMPLE 5

A solution of 6-fluoro-3,4-dichloro-2H-1-dihydro-benzopyran-2-one (15 g) in pyridine (15 ml) is maintained for 12 hours at room temperature; then the mixture is poured in water-ice and further 2N aqueous H$_2$SO$_4$ is added (pH 2.5). The precipitate is separated by filtration, dried under vacuum and crystallized from ethyl ether to yield 9.2 g of 6-fluoro-3-chloro-2-H-1-benzoypyran-2-one, m.p.=150°-152° C.

EXAMPLE 6

Under a nitrogen atmosphere, with all humidity excluded, 1M solution of DIBAH in toluene (25 ml) is added dropwise to a solution of 6-fluoro-2H1-benzopyran-2-one (2 g) in dry toluene, cooled at 70° C., in 40 minutes. The mixture is stirred at 65°-70° C. for 15 minutes to complete the reaction; then moist ethyl ether (20 ml) is added. The mixture is heated at room temperature and water (0.5 ml) is further added. After addition of dry Na$_2$SO$_4$ (15 g) followed by stirring for 3 hours at room temperature, the mixture is filtered and the organic phase is evaporated. The residue is crystallized from cyclohexane yielding 1.92 g of 6-fluoro-2H-1-benzopyran-2ξ-ol, m.p.=128°-131° C.

EXAMPLE 7

Destroying the excess reagent as in procedure of example 6 by a 2M solution of 2-propanol in toluene, the separated compound is 6-fluoro-2H-1-benzopyran-2-isopropoxy. The same compound is obtained starting from 6-fluoro-2H-1-benzopyran-2-ol (0.65 g) and isopropanol (5 ml) in the presence of 0.03 g of p-toluenesulfonic acid. After 3 hours at room temperature, pyridine (0.1 ml) is added and the mixture is evaporated to dryness. The residue is partitioned with ethyl ether and 5% aqueous NaH—CO$_3$, the organic phase is washed with water to neutral. After drying on Na$_2$SO$_4$ and evaporation of the solvent, 0.25 g of crystalline compound is isolated.

EXAMPLE 8

A mixture of p-fluoro-phenol (56 g), ethyl acetoacetate (64 ml) and sulphuric acid is heated at 90° C. for 3 hours; then it is poured in ice and water (400 ml). The aqueous phase is decanted and the precipitate is dissolved in methylene chloride. The organic phase is washed with water, 5% aqueous sodium hydrogen carbonate and water, until the washings are neutral. After drying on Na$_2$SO$_4$ and evaporation of the solvent, the residue is crystallized from isopropyl ether affording 12 g of 6-fluoro-4-methyl-2H-1-benzopyran-2-one, m.p.=162°-164° C. Following the same procedure but using ethyl-3-oxo-pentanoate, methyl 3-phenyl-3-oxo propionate, ethyl-3-oxo-hexanoate and ethyl 3-oxo-5-methyl heptanoate instead of ethylacetoacetate, the following fluoro coumarins are obtained:
6-fluoro-4-ethyl-2H-1-benzopyran-2-one
6-fluoro-4-phenyl-2H-1-benzopyran-2-one
6-fluoro-4-propil-2H-1-benzopyran-2-one
6-fluoro-4-isopropil-2H-1-benzopyran-2-one

EXAMPLE 9

Following the same procedure of example 1 but using 2-m-fluoro-phenol, o-fluoro-phenol, 2,4-difluoro-phenol, 2-chloro-4-fluoro-phenol, 2-bromo-4-fluoro-phenol and 2-iodo-4-fluoro-phenol instead of p-fluoro-phenol, the following fluoro coumarins are obtained:
8-fluoro-2H-1-benzopyran-2-one
7-fluoro-2H-1-benzopyran-2-one m.p.=158°-160° C.
6-difluoro-2H-1-benzopyran-2-one
6-fluoro-8-chloro-2H-1-benzopyran-2-one
6-fluoro-8-bromo-2H-1-benzopyran-2-one 6-fluoro-8-iodo-2H-1-benzopyran-2-one

EXAMPLE 10

A solution of 4.5 g of 6-fluoro-4-methyl-2H-1-benzopyran-2-one in chloroform (60 ml) is heated with bromine (2.6 g) at reflux temperature under lightening. After 5 hours the reaction is stopped and the excess reagent is destroyed by treatment with 5% aqueous sodium sulfite. The reaction mixture is worked-up in the usual way and the crude material (about 6 g) is dissolved in pyridine (10 ml) at room temperature for 2 hours. The reaction mixture is poured in ice-water acidified to pH 2.5 with 4N $H_2SO_4$ and extracted with ethylether. The organic phase after the usual work-up yields a crude material which is filtered on short column of $SiO_2$ eluting with methylene chloride. The eluates are collected, the solvent is evaporated to dryness and the residue crystallized from ethylether affords 3.5 g of 6-fluoro-4-bromomethyl-3-bromo-2H-1-benzopyran-2-one, m.p.=125°-127° C. A solution of this compound (1.5 g) in dimethoxyethane is stirred with a 2N solution of zinc borohydride in ethylether (2 molar equivalents). The excess of the reagent is destroyed by cautious adding of water, washed with 2N sulphuric acid, then with water. The solvents are evaporated to dryness, affording 0.74 g of 6-fluoro-4-methyl-3-bromo-2H-1-benzopyran-2-one. Using chlorine instead of bromine with the same procedure, the following 6-fluoro-coumarins are obtained:
6-fluoro-4-chloromethyl-3-chloro-2H-1-benzopyran-2-one
6-fluoro-4-methyl-3-chloro-2H-1-benzopyran-2-one.

EXAMPLE 11

Following the same procedure of example 6, but using 6-fluoro-4-bromethyl-3-bromo-2H-1-benzopyran-2-one and 6-fluoro-4-chloromethyl-3-chloro-2H-benzopyran-2-one instead of 6-fluoro-2H-1-benzopyran-2-one and using 2.2M equivalents of DIBAH as the reducing agent, the following compounds are obtained:
6-fluoro-4-methyl-3-bromo-2H-1-benzopyran-2-one
6-fluoro-4-methyl-3-chloro-2H-1-benzopyran-2-one

EXAMPLE 12

Following the same procedure of examples 3 and 10, but starting from 8-fluoro, 6-fluoro-8-chloro and 6-fluoro-8-bromo-2H-1-benzopyran-2-one, with an excess of bromine at reflux temperature under artificial 160 Watt lamp and treating the crude polibromo intermediate compounds directly with pyridine in order to have dehydrohalogenation, the following 3-bromo-fluoro coumarin compounds are obtained:
3-bromo-8-fluoro-2H-1-benzopyran-2-one
3-bromo-6-fluoro-8-chloro-2H-benzopyran-2-one
3,8-dibromo-6-fluoro-2H-1-benzopyran-2-one

EXAMPLE 13

Following the same procedure of example 12, but starting from a chlorine solution in $CCl_4$ instead of bromine and using the procedure of examples 3, 4, 5, 10, the following coumarins are obtained:
3-chloro-8-fluoro-2H-1-benzopyran-2-one
3,8-dichloro-6-fluoro-2H-1-benzoypyran-2-one
3-chloro-6-fluoro-8-bromo-2H-1-benzopyran-2-one
3-chloro-4-chloromethyl-6-fluoro-2H-1-benzopyran-2-one
3-chloro-4-methyl-6-fluoro-6-fluoro-2H-1-benzopyran-2-one

EXAMPLE 14

Following the same procedure of example 6, but using 3-bromo and 3-chloro-substituted 6-fluoro-2H-1-benzopyran-2-one and destroying the excess reagent with moist ethylether and water, the following lactols are obtained:
6-fluoro-3-bromo-2H-1-benzopyran-2-ol
6-fluoro-3-chloro-2H-1-benzopyran-2-ol

EXAMPLE 15

Under a nitrogen atmosphere, with exclusion of humidity, 1M solution of DIBAH in toluene (24 ml) is added dropwise to a solution of 3,4-dibromo-6-fluoro-2H-1-dihydro-benzopyran-2-one (3.25 g) cooled at 70° C. in 30 minutes. The mixture is stirred at −65°:−70° C. for 30 minutes, the excess reagent is destroyed by adding moist ethylether and water (0.5 ml). The mixture is warmed at room temperature, heated under stirring with anhydrous magnesium sulphate, filtered and evaporated to dryness, affording 3,12 g of 3,4 dibromo-6-fluoro-2H-1-dihydro-benzopyran-2-ol. A sample of 1 g of this crude material is dissolved in acetone (5 ml), the solution is added with NaI (0.8 g) and maintained at room temperature for a night. The red solution is treated with aqueous sodium sulfite, diluted with water. The separate material is crystallized from cyclohexane to yield 6-fluoro-2H-1-benzopyran-2-ξ-ol. Another sample of 1 g of the above crude lactol is dissolved in pyridine (4 ml) and, after 2 hours, the reaction is diluted with aqueous 2N sulfuric acid and ice. After extraction with ethylether and the usual work-up, it is obtained 6-fluoro-3-bromo-2H-1-benzopyran-2ξ-ol.

EXAMPLE 16

A mixture of 6-fluoro-2H-1-benzopyran-2ξ-ol (0.5 g) and diethylamino ethanol (1.5 ml) and catalytic amount of p-toluensulfonic acid are maintained at room temperature for 3 days. After evaporation in high vacuum of the excess reagent, the dark residue is filtered through a short column on $SiO_2$ eluating with ethylether-pyridine 100:0.5. The eluate is evaporated to dryness to afford 6-fluoro-2H-1-benzopyran-2ξ-diethylaminoethoxy.

What is claimed is:

1. A compound of the formula

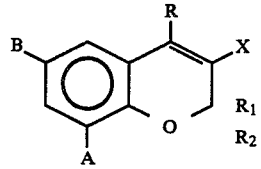

wherein:
A is hydrogen, fluorine, chlorine or bromine;
B is fluorine, or when A is fluorine B may be hydrogen;
R is hydrogen, $C_1$–$C_8$ branched or unbranched alkyl, or phenyl;
X is hydrogen, chlorine or bromine;
one of $R_1$ and $R_2$ is hydrogen and the other is hydroxy or $C_1$–$C_7$ branched or unbranched alkoxy unsubstituted or substituted by a di($C_1$–$C_2$-alkyl)amino group, or $R_1$ and $R_2$, taken together with the carbon atom to which they are linked, form the group =C=O; with the proviso that, when R and X are both hydrogen, and

is a =C=O group, and one of the groups A, B is fluorine, the other one is different from hydrogen.

2. A compound according to claim 1 wherein R is —(CH$_2$)$_n$—CH$_3$ or

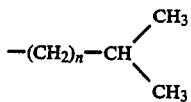

wherein n is 1 to 5.

3. A compound according to claim 1 or claim 2 wherein one of R$^1$ and R$^2$ is C$_{1-7}$ branched or unbranched alkyl substituted by dimethylamino or diethylamino.

4. A compound according to claim 1 selected from the group consisting of:
6-fluoro-4-methyl-2H-1-benzopyran-2-one
6-fluoro-4-ethyl-2H-1-benzopyran-2-one
6-fluoro-3-bromo-2H-1-benzopyran-2-one
6-fluoro-3-chloro-2H-1-benzopyran-2-one
6-fluoro-4-methyl-3-chloro-2H-1-benzopyran-2-one
6,8-difluoro-2H-1-benzopyran-2-one
6-fluoro-4-phenyl-2H-1-benzopyran-2-one
6-fluoro-4-methyl-3-bromo-2-H-1-benzopyran-2-one
8-fluoro-3-bromo-2H-1-benzopyran-2-one
6-fluoro-2ξ-hydroxy-2H-1-benzopyran
6-fluoro-2ξ-methoxy-2H-1-benzopyran
6-fluoro-2ξ-ethoxy-2H-1-benzopyran
6-fluoro-2ξ-(2'-dimethylaminoethoxy)-2H-1-benzopyran
6-fluoro-2ξ-(2'-diethylaminoethoxy)-2H-1-benzopyran
6-fluoro-2ξ-isopropoxy-2H-1-benzopyran
6-fluoro-3-bromo-2ξhydroxy-2H-1-benzopyran
6-fluoro-3-bromo-2ξ-methoxy-2H-1-benzopyran.

* * * * *